(12) United States Patent
Khanna

(10) Patent No.: US 6,660,007 B2
(45) Date of Patent: Dec. 9, 2003

(54) LAMINOPLASTY FIXATION SYSTEM

(75) Inventor: Rohit Kumar Khanna, Daytona Beach, FL (US)

(73) Assignee: Rohit K. Khanna, Daytona Beach, FL (US)

( * ) Notice: Subject to any disclaimer, the term of this patent is extended or adjusted under 35 U.S.C. 154(b) by 0 days.

(21) Appl. No.: 10/299,624

(22) Filed: Nov. 19, 2002

(65) Prior Publication Data

US 2003/0125740 A1 Jul. 3, 2003

Related U.S. Application Data

(63) Continuation of application No. 10/035,281, filed on Jan. 3, 2002.

(51) Int. Cl.[7] .......................... A61B 17/56; A61B 17/58; A61F 2/30
(52) U.S. Cl. ............................................. 606/61; 606/63
(58) Field of Search .............................. 606/60, 61, 62, 606/71, 72, 69, 90; 623/17.11, 17.16

(56) References Cited

U.S. PATENT DOCUMENTS

| 5,620,448 | A | * | 4/1997 | Puddu | 606/87 |
|---|---|---|---|---|---|
| 5,888,223 | A | * | 3/1999 | Bray, Jr. | 623/17.16 |
| 5,980,572 | A | * | 11/1999 | Kim et al. | 623/17.16 |
| 6,066,175 | A | * | 5/2000 | Henderson et al. | 623/17.11 |
| 6,080,157 | A | * | 6/2000 | Cathro et al. | 606/61 |
| 6,235,059 | B1 | * | 5/2001 | Benezech et al. | 623/17.16 |
| 6,241,771 | B1 | * | 6/2001 | Gresser et al. | 623/17.16 |
| 6,544,266 | B1 | * | 4/2003 | Roger et al. | 606/70 |

\* cited by examiner

Primary Examiner—Pedro Philogene
Assistant Examiner—David A Bonderer

(57) ABSTRACT

Fixation devices for stabilization and fusion of the lamina after laminoplasty are described. The device comprises of a plate with several holes that receive bone fasteners. The plate is curved at the ends to contour to the vertebral structure and has a spacer in the middle to engage the displaced lamina in a fixed position. Several fixation devices for dynamically stabilizing the lamina after either the open door, double door or expansive laminoplasty technique are provided.

26 Claims, 4 Drawing Sheets

LAMINOPLASTY FIXATION SYSTEM

PARENT CASE TEXT

This is a continuation of U.S. Ser. No. 10/035,281, filed Jan. 3, 2002

BACKGROUND OF THE INVENTION

Cervical stenosis with spinal cord compression and consequent myelopathy is a very common problem encountered by the spine surgeon. The usual cause of multilevel cervical stenosis is spondylosis and/or ossification of the posterior longitudinal ligament. Surgical decompression either through an anterior or posterior approach can be undertaken.

An anterior approach usually involves multilevel corpectomy with fusion and stabilization. The main drawback of this technique is the increased time and complexity of the procedure as well as the risk of pseudoarthrosis and accelerated degeneration at the levels above and below the fusion.

A posterior approach has traditionally involved a simple laminectomy, laminectomy with facet fusion, or more recently laminoplasty. The drawback of a simple laminectomy is the risk of late clinical deterioration form either kyphosis or postlaminectomy scar formation. Laminectomy with facet fusion decreases the risk of kyphosis but it also decreases the range of motion in the spine and increases the risk of accelerated degeneration at the levels above and below the fusion.

Laminoplasty either through open door or double door technique developed more recently provides greater stability and range of motion when compared with laminectomy alone. This technique entails laminoplasty for decompression with laminar fusion with allo- or autograft bone and/or fixation with a plate. The principle behind laminar fusion and fixation is that it maintains the decompression following laminoplasty as well as the displaced lamina in a fixed position thereby providing stabilization also.

U.S. Pat. No. 6,080,157 to Cathro et al. describes an implant to stabilize the lamina after an open door laminoplasty technique. A major limitation of this implant and technique is that a single implant extends to all the laminoplasty levels and does not provide well for lamina fusion, thereby being susceptible to stress fatigue. U.S. Pat. No. 5,980,572 to Kim et al. describes an implant to stabilize the lamina after a double door laminoplasty technique. This implant also does not provide well for lamina fusion and is susceptible to stress fatigue. U.S. patent application Ser. No. 10/035,281, filed by the author, describes several laminar fixation plates with and without a bone spacer that allow for lamina fixation and fusion.

The present invention is an apparatus for use in either the open door or double door laminoplasty technique to fuse and stabilize the lamina in the spine thereby preserving the range of motion as well as maintaining stability.

SUMMARY OF THE INVENTION

The present invention relates a laminar fusion and fixation system following either open door or double door laminoplasty technique. This system with the bone fusion spacer and plate reduces surgical time and simplifies laminar fusion and fixation after laminoplasty.

The lamina fixation device consists of a plate contoured at each end with a hollow spacer in the middle with variable length but uniform width and thickness specific for the cervical, thoracic or lumbar spine. The contoured design of the plate allows screw placement in the lamina or spinous process on one side and the facet on the other side. The spacer edges can be straight or contoured with a notch to allow securement to the lamina on one side and the lateral mass or facet on the other side. This implant is made of titanium or similar alloy with magnetic resonance imaging compatibility. The hollow spacer can be packed with allograft or autograft bone to provide for lamina fusion. Alternatively, the implant can be made of allograft bone or hydroxyapatite or similar absorbable material.

In another embodiment, the lamina fixation device is a plate and spacer construct designed for laminar fusion and fixation following double door laminoplasty. The hollow spacer in the middle of the plate allows for laminar fusion in the decompressed position once packed with either allograft bone, autograft bone, or bone morphogenic protein and with the plate design bent on either end securing the graft to the lamina and/or the facets on both sides.

The procedure as would be undertaken with the use of the laminoplasty fixation system is described as follows. An open door laminoplasty entails creating a gutter at the junction of the lamina and medial aspect of the facet on both sides with the use of a drill. On the side of the laminoplasty opening, the drilling is carried through into the canal or the opening completed with a small kerrison rongeur. At the other side, the inner cortex at the lamina and facet junction is not drilled. The lamina at the open end is elevated and the spinous process pushed away in order to create a greenstick osteotomy and allow for the laminoplasty decompression. Typically, at least one centimeter of distraction between the lamina and the facet provides for a good spinal decompression. In order to maintain the position of the lamina, the pre-contoured laminar fixation plate/spacer construct of appropriate size is positioned between the lamina and the facet. The spacer maintains the displaced position of the lamina and the plates with the contoured ends secure the construct via screws to the lamina and facet.

Another variation on the open door laminoplasty is the expansive laminoplasty most suited for the thoracolumbar spine. In this method, the lamina on either side at the junction of the facets are drilled and opened. A lateral spinal canal recess decompression and/or foraminotomy is undertaken and the lamina replaced with the spacer/plate construct on both sides.

A double door laminoplasty is created by drilling on each side at the laminar and facet junction the outer laminar cortex and sparing the inner laminar cortex. The spinous process is resected and a midline gutter is also created which extends through the inner cortex which can be opened with a small kerrison rongeur. The lamina on either side are lifted and opened creating a greenstick osteotomy on each side. In order to maintain the decompressed position of the lamina, the spacer/plate construct is placed. The plate can either be fixated with screws to the lamina or the facets on both sides

BRIEF DESCRIPTION OF THE DRAWINGS

A better understanding of the present invention will be had after a reading of the following detailed description taken in conjunction with the accompanying drawings wherein.

DETAILED DESCRIPTION OF THE EMBODIMENTS

Figure 1:
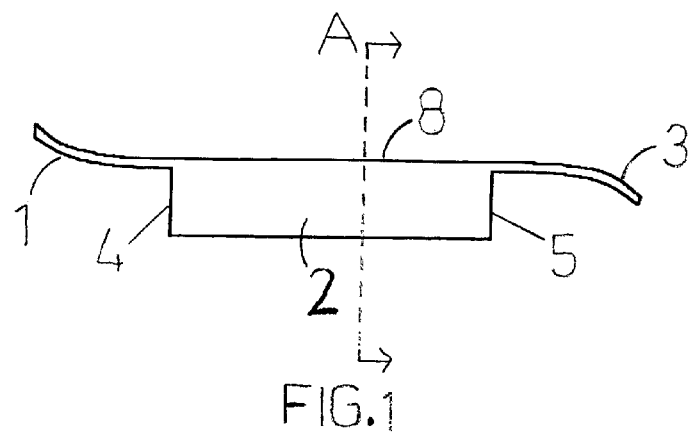
FIG. 1 is a side view of the plate
Figure 2:
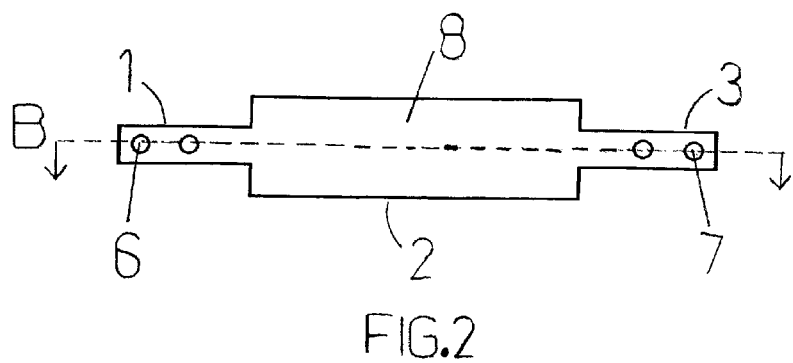
FIG. 2 is a top view of the plate
Figure 3:
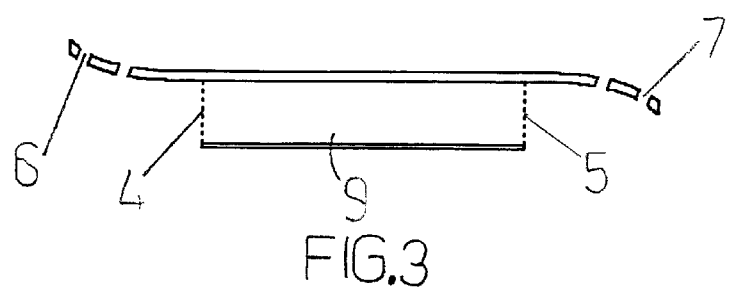
FIG. 3 is a cross sectional side view of the plate taken along line B in FIG. 2
Figure 4:
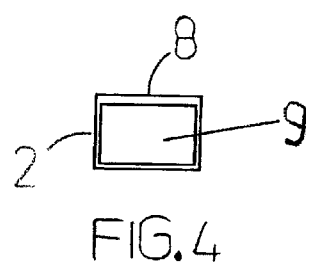
FIG. 4 is a cross sectional view of the plate taken along line A in FIG. 1

In one embodiment of the laminoplasty fixation device as illustrated in FIGS. 1 to 4, the device has a rectangular spacer in the middle with a top surface 8, longitudinal spacer side edge 2, an end side 4 that engages with the facet end, and an end side 5 that engages with the displaced lamina edge. The plates at the distal ends are curved upwards 1 at one end with screw holes 6 to allow fixation to the facet via a screw and curved downwards 3 with screw holes 7 to allow fixation to the lamina via a screw. The rectangular spacer in the middle is hollow 9 with a top side 8 contiguous with the plates 1 and 2 at both ends with screw holes 6 and 7. The hollow spacer has open end sides 4 and 5 and a side edge 2. The spacer can be packed with a fusion material like allograft or autograft bone, bone morphogenic protein, or hydroxyapatite to fuse the lamina in the fixed position provided by the device.

Figure 5:
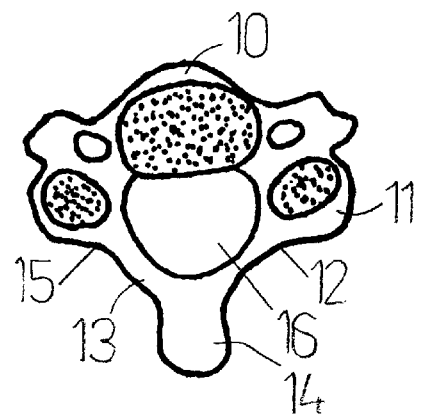
FIG. 5 is a top view of a vertebra
Figure 6:
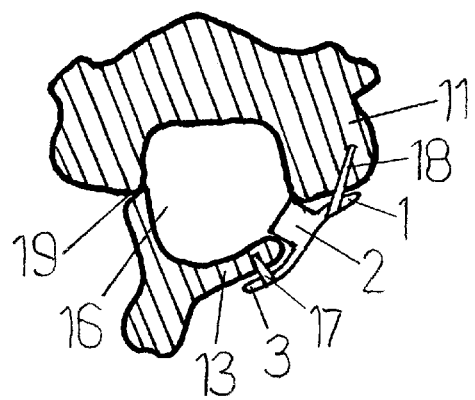
FIG. 6 is a cross section of the vertebra following open door laminoplasty with the plate in place

A top view of a vertebra is illustrated in FIG. 5 with vertebral body 10, facet 11, junctions of the facet and lamina 12 and 15, lamina 13, spinous process 14, and spinal canal 16. For the open door technique of laminoplasty, as illustrated in FIG. 6, a bicortical opening at the junction of the lamina and facet on one side and a unicortical groove 19 on the other side with a greenstick fracture is created for the laminar displacement. A laminar fixation device is placed between the facet 11 and lamina 13 to maintain the repositioned shape of the lamina that provides decompression of the spinal canal 16. The laminar fixation device has a spacer 2 with a curved plate 1 at one end which secures the fixation device to the facet 11 with a screw 18 and a curved plate 3 at the other end which secures the fixation device to the lamina 13 with a screw 17. The spacer 2 can be solid or hollow to allow for packing with a bone fusion material like bone or bone morphogenic protein.

Figure 7:
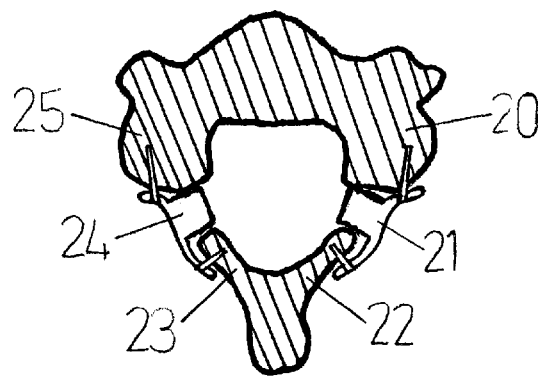
FIG. 7 is a cross section of the vertebra following expansive laminoplasty with the plates in place
Figure 8:
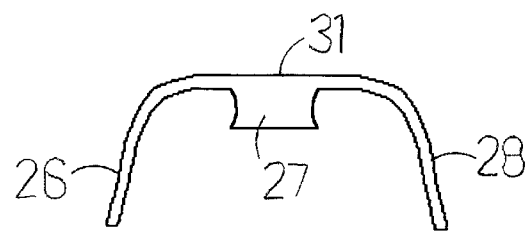
FIG. 8 is a side view of another embodiment of the plate
Figure 9:
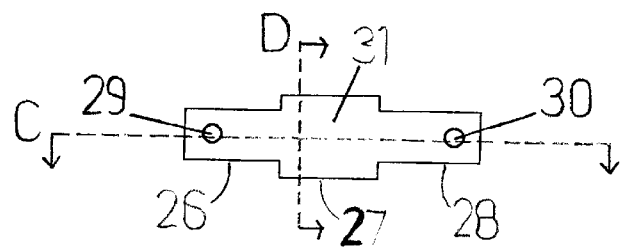
FIG. 9 is a top view of the plate
Figure 10:
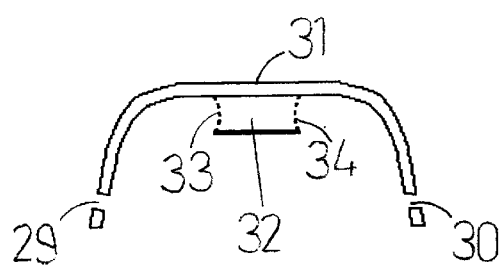
FIG. 10 is a cross sectional side view of the plate taken along line C in FIG. 9
Figure 11:
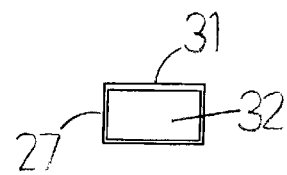
FIG. 11 is a cross sectional view of the plate taken along line D in FIG. 9

For the expansive laminoplasty technique as illustrated in FIG. 7, the laminoplasty fixation device is used on both sides. On one side, the fixation device 21 is implanted between the facet 20 and lamina 22, whereas on the other side, the fixation device 24 is implanted between the facet 25 and lamina 23.

Figure 12:
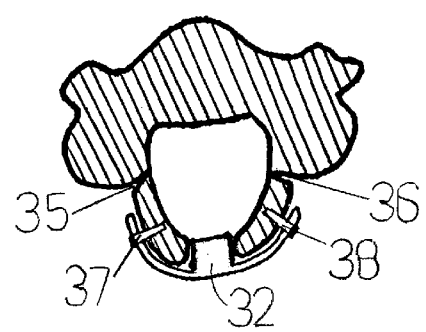
FIG. 12 is a cross section of the vertebra with the plate in place
Figure 13:
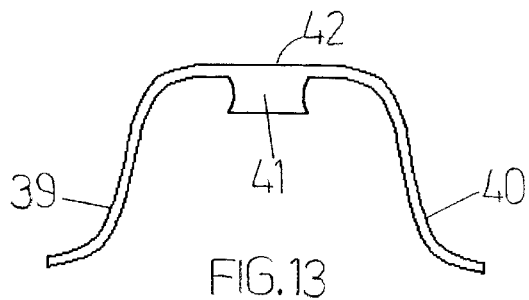
FIG. 13 is a side view of another embodiment of the plate
Figure 14:
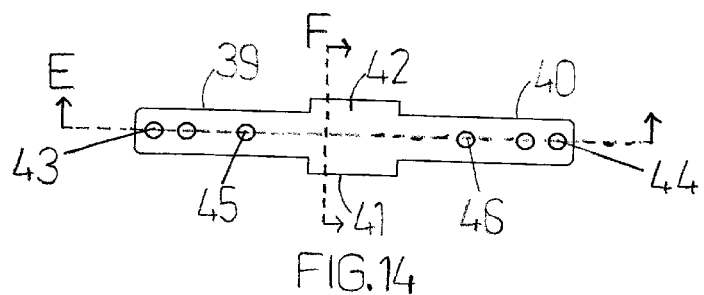
FIG. 14 is a top view of the plate
Figure 15:
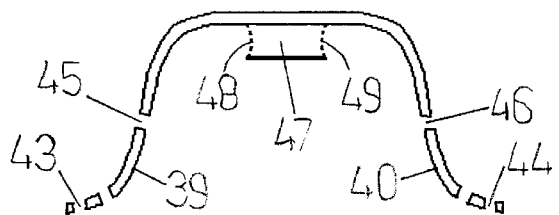
FIG. 15 is a cross sectional side view of the plate taken along line E in FIG. 14
Figure 16:
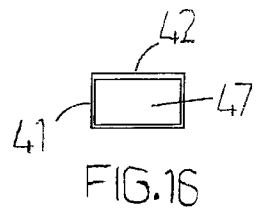
FIG. 16 is a cross sectional view of the plate taken along line F in FIG. 14

Another embodiment of the laminoplasty fixation device is illustrated in FIGS. 8 to 11. The fixation device has a U-shape with distal ends 26 and 28 and a spacer 27 in the middle. The plates at the distal ends are curved with screw holes 29 and 30 to allow fixation to the lamina via screws. The rectangular spacer in the middle is hollow 32 with a top side 31 contiguous with the plates 26 and 28 at both ends. The hollow spacer has open end sides 33 and 34 and a side edge 27. The spacer can be packed with a fusion material like allograft bone, autograft bone, or bone morphogenic protein. The trap door laminoplasty technique as shown in FIG. 12 involves removal of the spinous process and creation of unicortical laminoplasty grooves 35 and 36 at the junction of the lamina and facet on both sides. The displaced lamina are then maintained in that position with a lamina fixation device with a spacer in the middle 32. The fixation device also has plates with bone screw receiving holes that allow fixation of the plate with bone screws 37 and 38 securing the construct to the lamina.

Figure 17:
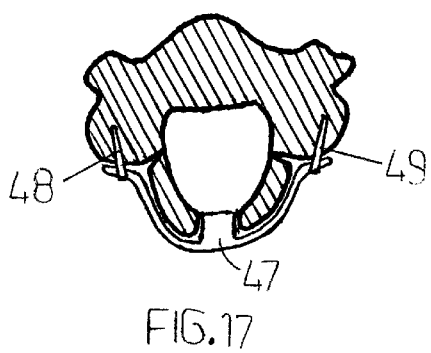
FIG. 17 is a cross section of the vertebra with the plate in place

In another embodiment of the laminoplasty fixation device for the trap door laminoplasty technique as illustrated in FIGS. 13 to 16, the plate has a top surface 42 with bone screw holes 43 and 44 for fixation to the facets and screw holes 45 and 46 for further fixation to the lamina if needed. The plate also has curved ends 39 and 40 contoured for fixation to the facets. The rectangular spacer 41 attached to the plate in the center has open side ends 48 and 49 with a hollow center 47. FIG. 17 illustrates the lamina fixation device in place following an open door laminoplasty. The displaced lamina are then maintained in that position with a lamina fixation device with a spacer in the middle 47 with the plate fixated to the facets through bone screws 48 and 49.

The length of the plates as well as the spacer can vary depending on the laminar displacement desired by the surgeon with either the open door or trap door laminoplasty technique.

While the present invention has been described in conjunction with preferred embodiments and methods, it is intended that the description and accompanying drawings shall be interpreted as only illustrative of the invention. It is evident that those skilled in the art may make numerous uses and modifications of and departures from the specific embodiments described herein without departing from the inventive concept.

References

| U.S. Patent Documents | | |
| --- | --- | --- |
| 5980572 | November 1999 | Kim et al. |
| 6080157 | June 2000 | Cathro et al. |
| 6241771 | June 2001 | Gresser et al. |

What is claimed is:

1. Bone fixation device for the lamina of the spine after laminoplasty comprising of: i) an elongated plate defining a longitudinal axis with curvature at the ends, downward for fixation to a lamina and upward for fixation to a facet by means of a screw through bone screw receiving holes at each end of the said plate, and ii) a rectangular shaped spacer in the middle of the plate with ends which are able to engage and maintain the displaced edges of a lamina in a fixed position.

2. Bone fixation device of claim 1 wherein the elongated plates are flexible to allow bending to a specific anatomical contour at each end for various laminoplasty techniques.

3. Bone fixation device of claim 1 wherein said spacer has straight sides at both ends perpendicular to the longitudinal axis and prior to the curvature at both ends of the said plate.

4. Bone fixation device of claim 3 wherein said spacer is hollow with openings at both side ends; the hollow spacer can be packed with a bone fusion material selected from the group consisting of autograft bone, allograft bone, xenograft bone, bone morphogenic protein, and hydroxyapatite.

5. Bone fixation device of claim 1 wherein said spacer has L-shaped sides at one or both ends perpendicular to the longitudinal axis and prior to the curvature at both ends of the said plate.

6. Bone fixation device of claim 5 wherein said spacer is hollow with openings at both side ends; the hollow spacer can be packed with a bone fusion material selected from the group consisting of autograft bone, allograft bone, xenograft bone, bone morphogenic protein, and hydroxyapatite.

7. Bone fixation device of claim 1 wherein said spacer has concave sides at both ends perpendicular to the longitudinal axis and prior to the curvature at both ends of the said plate.

8. Bone fixation device of claim 7 wherein said spacer is hollow with openings at both side ends; the hollow spacer can be packed with a bone fusion material selected from the group consisting of auto graft bone, allograft bone, xenograft bone, bone morphogenic protein, and hydroxyapatite.

9. Bone fixation device of claim 1 wherein said device is made from a biocompatible material selected from the group consisting of titanium, titanium alloys, surgical steel, polymeric material, ceramic material, carbon fiber composite, resorbable material, polyglyconate, allograft bone, xenograft bone, and hydroxyapatite.

10. Bone fixation device for the lamina of the spine after laminoplasty comprising of: i) an elongated plate defining a longitudinal axis with bone screw receiving holes at the ends wherein said plate has a U-shape to allow for fixation to the lamina via screws, and ii) a spacer in the middle of the plate which is able to engage and maintain the displaced edges of two-lamina in a fixed position.

11. Bone fixation device of claim 10 wherein said spacer has a rectangular shape with straight sides at both ends perpendicular to the longitudinal axis and prior to the curvature at both ends of the said plate.

12. Bone fixation device of claim 11 wherein said spacer is hollow with openings at both side ends; the hollow spacer can be packed with a bone fusion material selected from the group consisting of autograft bone, allograft bone, xenograft bone, bone morphogenic protein, and hydroxyapatite.

13. Bone fixation device of claim 10 wherein said spacer has concave sides at both ends perpendicular to the longitudinal axis and prior to the curvature at both ends of the said plate.

14. Bone fixation device of claim 13 wherein said spacer is hollow with openings at both side ends; the hollow spacer can be packed with a bone fusion material selected from the group consisting of autograft bone, allograft bone, xenograft bone, bone morphogenic protein, and hydroxyapatite.

15. Bone fixation device of claim 10 wherein said spacer has L-shaped sides at both ends perpendicular to the longitudinal axis and prior to the curvature at both ends of the said plate.

16. Bone fixation device of claim 15 wherein said spacer is hollow with openings at both side ends; the hollow spacer can be packed with a bone fusion material selected from the group consisting of autograft bone, allograft bone, xenograft bone, bone morphogenic protein, and hydroxyapatite.

17. Bone fixation device of claim 10 wherein said device is made from a biocompatible material selected from the group consisting of titanium, titanium alloys, surgical steel, polymeric material, ceramic material, carbon fiber composite, resorbable material, polyglyconate, allograft bone, xenograft bone, and hydroxyapatite.

18. Bone fixation device for the lamina of the spine after laminoplasty comprising of: i) an elongated plate defining a longitudinal axis with bone screw receiving holes at the ends wherein said plate has a U-shape in the middle and an inverse L-shaped curvature at the ends on both sides to allow for fixation to the facets via screws, and ii) a spacer in the middle of the plate which engages and maintains the displaced edges of a lamina in a fixed position.

19. Bone fixation device of claim 18 wherein said spacer has a rectangular shape with straight sides at both ends perpendicular to the longitudinal axis and prior to the curvature at both ends of the said plate.

20. Bone fixation device of claim 19 wherein said spacer is hollow with openings at both side ends; the hollow spacer can be packed with a bone fusion material selected from the group consisting of autograft bone, allograft bone, xenograft bone, bone morphogenic protein, and hydroxyapatite.

21. Bone fixation device of claim 18 wherein said spacer has concave ends at both sides perpendicular to the longitudinal axis and prior to the curvature at both ends of the said plate.

22. Bone fixation device of claim 21 wherein said spacer is hollow with openings at both side ends; the hollow spacer can be packed with a bone fusion material selected from the group consisting of autograft bone, allograft bone, xenograft bone, bone morphogenic protein, and hydroxyapatite.

23. Bone fixation device of claim 18 wherein said spacer has L-shaped sides at both ends perpendicular to the longitudinal axis and prior to the curvature at both ends of the said plate.

24. Bone fixation device of claim 23 wherein said spacer is hollow with openings at both side ends; the hollow spacer can be packed with a bone fusion material selected from the group consisting of autograft bone, allograft bone, xenograft bone, bone morphogenic protein, and hydroxyapatite.

25. Bone fixation device of claim 18 wherein said plate has a plurality of bone screw receiving holes throughout the plate.

26. Bone fixation device of claim 18 wherein said device is made from a biocompatible material selected from the group consisting of titanium, titanium alloys, surgical steel, polymeric material, ceramic material, carbon fiber composite, resorbable material, polyglyconate, allograft bone, xenograft bone, and hydroxyapatite.

* * * * *